US011207082B2

(12) United States Patent
Boukhris et al.

(10) Patent No.: US 11,207,082 B2
(45) Date of Patent: Dec. 28, 2021

(54) SURGICAL DRILL TYPE CUTTING TOOL

(71) Applicant: IMPLANTS DIFFUSION INTERNATIONAL, Montreuil (FR)

(72) Inventors: Gilles Boukhris, Paris (FR); Gildas Sebillet, Chatillon (FR); Gérard Boukhris, Paris (FR)

(73) Assignee: Implants Diffusion International, Montreuil (FR)

( * ) Notice: Subject to any disclaimer, the term of this patent is extended or adjusted under 35 U.S.C. 154(b) by 216 days.

(21) Appl. No.: 16/481,801

(22) PCT Filed: Jan. 22, 2018

(86) PCT No.: PCT/EP2018/051466
§ 371 (c)(1),
(2) Date: Jul. 29, 2019

(87) PCT Pub. No.: WO2018/145888
PCT Pub. Date: Aug. 16, 2018

(65) Prior Publication Data
US 2020/0029978 A1 Jan. 30, 2020

(30) Foreign Application Priority Data
Feb. 7, 2017 (FR) ...................................... 1770120

(51) Int. Cl.
A61B 17/16 (2006.01)
A61C 1/05 (2006.01)
(Continued)

(52) U.S. Cl.
CPC ........ *A61B 17/1644* (2013.01); *A61B 17/162* (2013.01); *A61B 17/1615* (2013.01); *A61C 1/055* (2013.01); *A61C 1/12* (2013.01); *A61C 3/02* (2013.01); *A61B 90/92* (2016.02); *A61B 90/94* (2016.02); *A61B 2017/1651* (2013.01); *A61B 2090/036* (2016.02); *A61B 2090/0807* (2016.02)

(58) Field of Classification Search
CPC ........................ A61B 17/16–1697; A61C 3/02
See application file for complete search history.

(56) References Cited

U.S. PATENT DOCUMENTS 4,710,075 A   12/1987  Davison
5,078,605 A * 1/1992  Sutter ................ A61B 17/1644
                                                           408/59
(Continued)

FOREIGN PATENT DOCUMENTS

EP        0991360 B1    3/2004
EP        1974680 A1    1/2008
(Continued)

*Primary Examiner* — Zade Coley
(74) *Attorney, Agent, or Firm* — Harness, Dickey & Pierce, PLC

(57) ABSTRACT

A surgical drill type cutting tool includes a shank and an active portion extending in the extension of the shank, with chip areas extending along the active portion, and a ring surrounding a part of the active portion, an inner surface of the ring engaging the active portion without closing off the chip areas, allowing irrigation fluid to provides useful irrigation over most of the length of the active portion of the surgical drill bit.

12 Claims, 1 Drawing Sheet

(51) Int. Cl.
  *A61C 1/12*  (2006.01)
  *A61C 3/02*  (2006.01)
  *A61B 90/00*  (2016.01)
  *A61B 90/92*  (2016.01)
  *A61B 90/94*  (2016.01)

(56) References Cited

U.S. PATENT DOCUMENTS

| | | | | |
|---|---|---|---|---|
| 5,839,897 | A * | 11/1998 | Bordes | B23B 51/02 |
| | | | | 433/165 |
| 6,235,035 | B1 | 5/2001 | Boukhris | |
| 6,641,395 | B2 * | 11/2003 | Kumar | A61B 17/1615 |
| | | | | 433/165 |
| 9,610,085 | B2 * | 4/2017 | Bjorn | A61B 17/1679 |
| 2002/0031745 | A1 * | 3/2002 | Kumar | A61C 8/0089 |
| | | | | 433/165 |
| 2003/0049586 | A1 * | 3/2003 | Kumar | A61C 8/0089 |
| | | | | 433/165 |
| 2006/0111724 | A1 * | 5/2006 | Yeung Wai Ping | A61C 8/0089 |
| | | | | 606/80 |
| 2008/0281343 | A1 * | 11/2008 | Dewey | A61B 17/32002 |
| | | | | 606/180 |
| 2009/0004625 | A1 * | 1/2009 | Esposti | A61B 17/176 |
| | | | | 433/165 |
| 2013/0218160 | A1 * | 8/2013 | Bjorn | A61B 17/1679 |
| | | | | 606/80 |
| 2018/0161124 | A1 * | 6/2018 | Huwais | A61B 90/03 |

FOREIGN PATENT DOCUMENTS

FR   2762776 A1   11/1998
FR   3002842 A1   12/2014

* cited by examiner

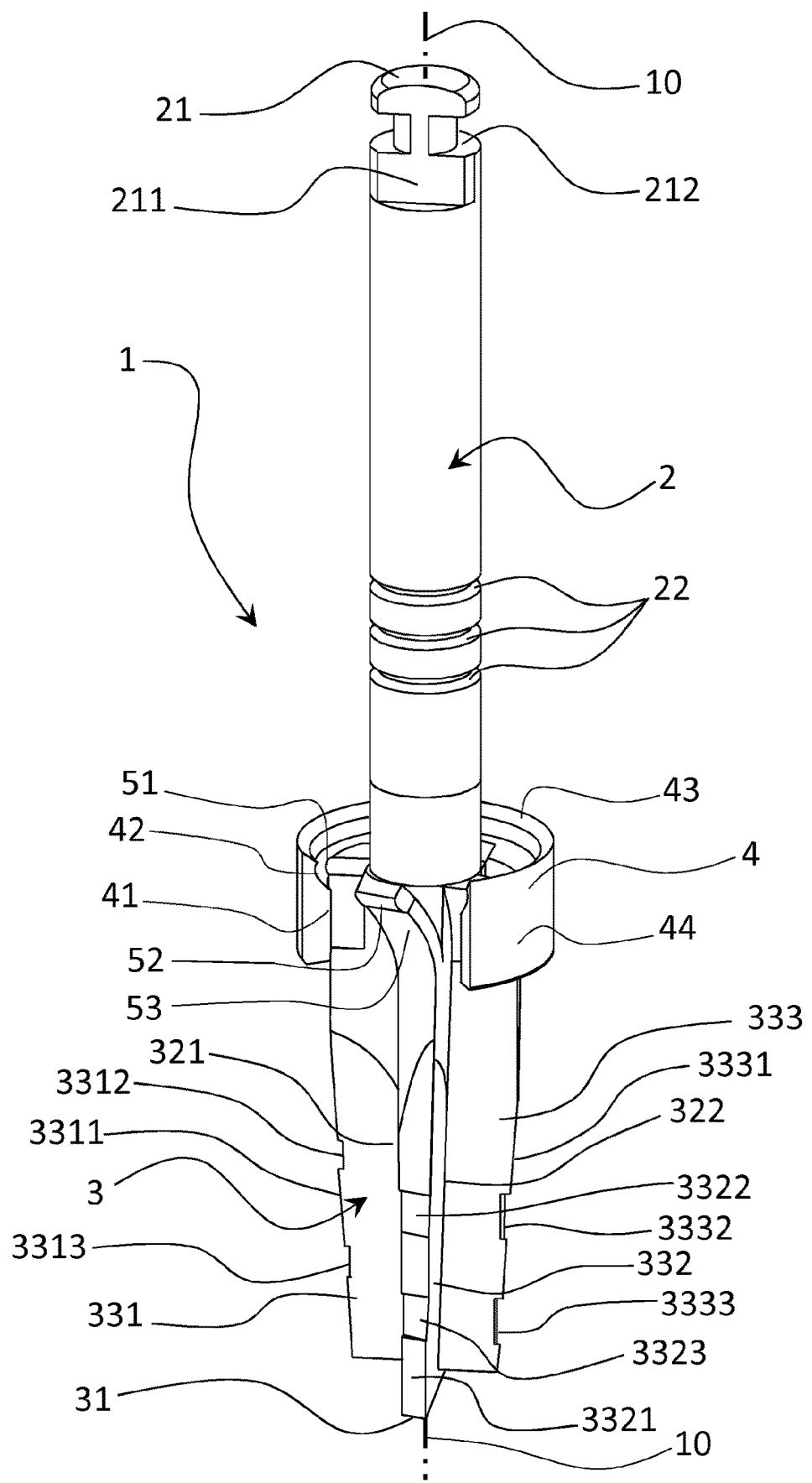

SURGICAL DRILL TYPE CUTTING TOOL

CROSS-REFERENCE TO RELATED APPLICATIONS

This application is a National Phase entry of International Application No. PCT/EP2018/051466, filed on Jan. 22, 2018, which claims priority to French Application No. 1770120, filed on Feb. 7, 2017, both of which are incorporated by reference herein.

TECHNICAL FIELD

The present invention relates to a rotary surgical drill type cutting tool designed to be carried by means such as a contra-angle handpiece.

BACKGROUND AND SUMMARY

Tools used in surgery include rotary cutting tools, commonly referred to as surgical drill bits, which are designed to be mounted on a contra-angle handpiece capable of driving them in rotation. Such surgical drill bits are commonly used in dental or endodontic surgery, or in bone surgery for instance in order to perform bone removal for bone grafting purposes. They conventionally comprise a shank, which is designed to be held by the contra-angle handpiece, and an active portion located on the extension of the shank and which is designed to be introduced into the bone or tooth of the patient. Some designs of contra-angle handpieces designed to receive surgical drill bits include irrigation systems which provide irrigation or cooling fluid to the surgical drill bit for cooling or lubricating it and/or for removing chips from the hole made by the surgical drill bit.

It is known, for example from European Patent EP 0991360 or from U.S. Pat. No. 4,710,075, to fit surgical drill bits with an abutment or stop having a diameter greater than the diameter of the active portion of the surgical drill bit. This abutment separates the active portion from the shank of the surgical drill bit, and thus limits penetration of the surgical drill bit to the desired depth. This abutment may also serve as an information medium, for example by its color or by inscribed indications allowing easy identification of the surgical drill bit.

It has however been found that when a surgical drill bit that is equipped with such an abutment is used with a contra-angle handpiece providing for supply of irrigation fluid, the abutment constitutes an obstacle hindering the flow of this irrigation fluid along the surgical drill bit, thus preventing good irrigation of the active portion of the surgical drill bit.

The invention aims to overcome these disadvantages of the prior art. More specifically, the present invention aims to provide a surgical drill bit having an abutment capable of limiting its penetration and the active portion of which can be satisfactorily irrigated by an irrigation fluid. A particular aim of the invention is to provide such a surgical drill bit capable of guiding the irrigation fluid so that it provides useful irrigation over most of the length of the active portion of the surgical drill bit. Another aim of the invention, in some of its embodiments, is to provide such a surgical drill bit that can be easily recognized by a practitioner.

These aims, as well as others that will emerge more clearly later, are achieved with the aid of a surgical drill bit type cutting tool comprising:
- a shank and an active portion located on an extension of said shank,
- means for retaining and holding the shank in rotation, a first end of the shank including a flat and a peripheral groove for this purpose,
- the active portion has a cruciform section, comprising four cutting lips separating four chip areas,
- a ring surrounding a part of said active portion, an inner surface of said ring engaging said active portion,
- that part of the active portion adjacent to the shank is surrounded by said ring which surrounds the outer contours of the drill bit formed by margin lands of the cutting lips of said active portion, without closing off said chip areas and thus without preventing the flow of fluid such as an irrigation or cooling product along the drill,
- an inner face of the ring has a concave groove open in the direction of the shank and is followed by an inclined portion of frusto-conical shape forming a face of said ring directed towards the shank, said concave groove and said inclined portion together forming a gullwing profile making it possible to concentrate irrigating or cooling fluid flowing along the shank of the drill in the direction of the said chip areas of the active portion.

According to an embodiment of the invention, the concave groove is a peripheral groove of a diameter greater than the diameter of the cutting lips and which is open on the face of the ring directed towards the shank. According to a further embodiment of the invention, the inner surface of the ring has a shape of a body of revolution. According to a further embodiment of the invention, the active portion has at least two chip areas extending along at least part of the active portion, the chip areas being separated by the cutting lips.

According to a further embodiment of the invention, the cutting lips of a part of the active portion surrounded by the ring exhibit locally a peripheral bulge, and an inner surface of the ring has a shape adapted to engage with the bulge. According to a further embodiment of the invention, the one or more chip areas have, on a part of the active portion surrounded by the ring, a helical orientation in a direction for driving a fluid present around the shank towards the active portion, when the cutting tool is rotated in its normal direction of rotation. According to a further embodiment of the invention, the ring comprises at least one portion forming a vane or a helix, oriented in a direction for driving a fluid present around the shank towards the active portion, when the cutting tool is driven in its normal direction of rotation.

According to a further embodiment of the invention, the ring is removably mounted on the active portion. According to yet a further embodiment of the invention, the active portion is configured to receive the ring at a plurality of positions or to accommodate a plurality of rings. According to yet a further embodiment of the invention, the ring is fixedly mounted on the active portion. According to yet a further embodiment of the invention, the ring is made of metallic material. According to yet a further embodiment of the invention, the ring carries visible signs, suitable for giving information to a practitioner.

BRIEF DESCRIPTION OF THE DRAWING

The invention will be better understood on reading the following description of preferred embodiments, provided by way of a simple diagrammatic and non-limiting example, and in conjunction with FIG. 1 which is a perspective view of a surgical drill bit in the form of a preferred embodiment of the invention, comprising a ring which is shown partly cutaway.

DETAILED DESCRIPTION

FIG. 1 shows a surgical drill bit type cutting tool. This surgical drill bit 1 conventionally comprises a shank 2, sometimes called a dental shank, together with an active portion 3 located on the extension of the shank 2.

The Shank

The shank 2 is designed to be inserted into and held in a contra-angle handpiece, or in any other instrument suitable for holding the surgical drill bit 1 and driving it in rotation. Conventionally, this shank 2 has a generally cylindrical shape, centered on an axis 10 referred to hereinafter as the drill axis. The shank 2 has, near its first end 21 forming an end of the surgical drill bit 1, a flat 211 and a peripheral groove 212 for retaining and rotating it in the contra-angle handpiece. In certain possible embodiments, the shank 2 may be provided with information for the practitioner, which may be in the form of a color code, for example in the form of circular markings, engravings such as peripheral striations, or signs indicating a reference or an item of information on the drill. Thus, the shank 2 shown in FIG. 1 has three peripheral striations 22, allowing it to be easily recognized by the practitioner.

The Active Portion

Shank 2 is extended beyond its second end opposed to its first end 21 by the active portion 3 of the surgical drill bit which extends to the tip 31 of the drill bit. Active portion 3 is designed to be introduced into the tooth or the bone of a patient, to perform a machining operation. In the embodiment shown, the active portion has a cruciform section, having four cutting lips separating four chip areas or flutes. Three of these cutting lips, bearing reference numerals 331, 332 and 333, are visible in FIG. 1. Each chip area or flute is defined between two adjacent cutting lips. Two of these chip areas are visible in FIG. 1: chip area 321 which extends between the cutting lip 331 and the cutting lip 332, and chip area 322 which extends between cutting lip 332 and cutting lip 333. In the embodiment shown, the four cutting lips extend substantially rectilinearly, in two perpendicularly intersecting planes along the axis of the drill 10.

However, in other embodiments of the invention, it is possible for the chip areas or flutes to have a helical orientation, the helix of which has, for example, an inclination of between 0° and 150°, in one direction or the other. Similarly, it is possible for the active portion 3 to have a different number of chip areas, one single chip area being necessary for implementing the proposed solution.

The outer surface of each cutting lip, respectively 331, 332 and 333, forms the marginal land, respectively 3311, 3321 and 3331, of the cutting lip. Over most of active portion 3, these marginal lands are inscribed in a frusto-conical envelope surface centered on the axis of drill 10. In other possible embodiments, this envelope surface may be cylindrical, cylindro-conical, conical, stepped, or any other shape known to those skilled in the art.

In the embodiment shown, indentations or teeth 3312, 3313, 3322, 3323, 3332 and 3333 are machined in the surface of the marginal lands 3311, 3321 and 3331. In other embodiments, the marginal lands may have different configurations. They may for example have grooves, which are helical or in planes perpendicular to the axis of drill 10. In general, the active portion 3 of the surgical drill bit may have any form known to those skilled in the art for such surgical drill bits.

The Ring

At its end opposed to the tip 31 of the surgical drill bit, the part of active portion 3 adjacent the shank 2 is surrounded by a ring 4. It should be noted that the ring 4 is shown cutaway in FIG. 1 in order to show its internal shape and the shape of the part of active portion 3 that it surrounds. The ring 4 shown in FIG. 1 thus actually exhibits a shape of a body of revolution centered on the axis of drill 10. Advantageously, ring 4 surrounds the outer contours of the surgical drill bit formed by marginal lands of the cutting lips of the active portion, without closing off the chip areas.

Thus, the presence of the ring 4 does not prevent the flow of fluid along surgical drill bit 1. A fluid flowing along shank 2 in the direction of the tip 31, for example under the effect of gravity, can thus flow easily along active portion 3, by penetrating into the chip areas to pass into the ring 4. This ring 4 can however comprise a turbine, oriented in a direction for driving a fluid present around said shank (2) towards the active portion (3), when said cutting tool is driven in its normal direction of rotation.

Ring 4, which preferably has a diameter greater than the maximum diameter of active portion 3, can serve as an abutment limiting the degree of penetration of active portion 3, and thereby rendering the use of the surgical drill bit 1 safe. Furthermore the ring 4 has the role when a turbine is used of protecting the soft tissues towards the action of rotation of the cutting blades. The surgical drill bit 1 comprising the ring 4 thus has the advantages of prior art drills provided with abutments or stops while allowing satisfactory irrigation of the active portion by an irrigation fluid.

The Top of the Active Portion

The part of the active portion which is surrounded by the ring 4 advantageously has a particular configuration. Thus, on the part of active portion 3 which adjoins the shank 2, the margin land of the cutting lips has a peripheral bulge, locally conferring a larger diameter on the envelope surface on which active portion 3 is inscribed. In FIG. 1, the bulges 51 and 52 respectively on the portions of the cutting lips 331 and 332 which adjoin shank 2 can be seen.

This bulge forms, advantageously, a support for the ring 4, which has a matching internal shape. Thus, the bulge prevents the ring 4 from shifting by sliding along surgical drill bit 1 in the direction of end 21. In other embodiments, the bulge may not appear. Consequently, active portion 3 may have other shapes, such as grooves, allowing translatory movement of ring 4 to be blocked. In still other embodiments, the ring may be fixed to active portion 3 by other means, for example by bonding.

Moreover, the chip areas and the cutting lips which separate them exhibit a helical shape locally at the part of active portion 3 which is surrounded by the ring 4. This helical shape is particularly visible in FIG. 1 through the inclination of portion 53 of cutting lip 322. The helix thus formed advantageously has an orientation providing for, when the surgical drill bit 1 is rotated in its normal direction of rotation, propulsion and sucking of irrigation fluid which is located around the shank 2 in order to propel it into the chip areas of active portion 3. Thus, the irrigation fluid is driven towards tip 31, with a speed which increases as the speed of rotation of the surgical drill bit 1 increases.

In other possible embodiments of the invention, the chip areas may not have the form of a helix. It is particularly possible, in a particular embodiment, for the ring 4 itself to have portions forming vanes or a helix, to obtain the same propulsion effect of irrigation fluid around shank 2 to the chip areas of active portion 3. It is also possible, in still other embodiments, for the irrigation fluid to flow in the chip areas only as a result of the propulsion conferred by the irrigation system of the contra-angle handpiece, or under the effect of gravity.

Inner Face of the Ring

The inner face of the ring 4, which is in contact with active portion 3 of the surgical drill bit, preferably has a form of a body of revolution. In the embodiment shown it has, over most of its length, a cylindrical shape 41 to match up with the surface of the marginal lands, which are inscribed on a cylindrical shape at this part of active portion 3.

At the level of the bulges 51 and 52 of the active portion, the inner face of the ring has a concave groove 42 allowing it to engage with the bulges 51 and 52. The groove is advantageously larger in size than the bulges, and is open in the direction of the shank 2. It is prolonged by an inclined portion 43, frusto-conical in shape, which forms the face of the ring 4 facing the shank 2. The concave groove 42 and the inclined portion 43 together form a sort of gullwing profile known especially for the shapes of aircraft wings or boat hulls. The profile which is open in a direction of shank 2 makes it possible to concentrate the irrigating or cooling fluid flowing along the shank 2 of the surgical drill bit 1 in the direction of the chip areas of active portion 3.

In other possible embodiments, the inner face of the ring may have other shapes. It may for example have one or more concave or convex grooves.

External Shape of the Ring

The ring may be made of metal or any other suitable material. Its thickness, in the direction defined by drill axis 10 is advantageously greater than 1 millimeter and may be several millimeters. Its diameter is advantageously greater than 2 millimeters. The ring 4 can be of the natural color of the material that forms it, or it can be colored with any other color to constitute a sign for recognition by the practitioner. Its outer face 44, in the embodiment shown, is cylindrical. The outer face may advantageously receive any sign allowing it to be identified, such as horizontal or vertical streaks, signs or colors, to inform the practitioner of the serial number, batch, length of the surgical drill bit, its reference numeral, its active length or diameter, or more generally to give any useful information to the practitioner.

It is also possible, in a particular embodiment of the invention, for the ring 4 to have lateral bores between its inner face and its outer face, to allow the passage of irrigation fluid. The ring 4 can be assembled onto the active portion of the drill by press or snap-in fitting. Assembly can be definitive, to make the ring a permanent fixture, or can be reversible to make the ring removable. In some embodiments, it is possible for the surgical drill bit to be configured to receive the ring in a plurality of positions on active portion 3, or to accommodate a plurality of rings. In some possible embodiments, the bulges of the active portion may be used to engage with a removable ring or, alternatively, with a stop or an abutment of a different type.

What is claimed is:

1. A surgical drill bit type cutting tool comprising:
   a shank and an active portion located on an extension of the shank;
   a retainer located at a first end of the shank comprising a flat and a peripheral groove, operably retaining and holding the shank in rotation;
   the active portion having a cruciform section, comprising four cutting lips separating four chip areas;
   a ring surrounding a part of the active portion, and an inner surface of the ring engaging the active portion;
   a part of the active portion adjacent to the shank being surrounded by the ring which surrounds the outer contours of the drill bit formed by margin lands of the cutting lips of the active portion, without closing off the chip areas and thus without preventing the flow of fluid such as an irrigation or cooling product along the drill;
   an inner face of the ring including a concave groove open in the direction of the shank and being followed by an inclined portion of frustoconical shape forming a face of the ring directed towards the shank, the concave groove and the inclined portion together forming a gullwing profile making it possible to concentrate irrigating or cooling fluid flowing along the shank of the drill in a direction of the chip areas of the active portion.

2. The surgical drill bit type cutting tool according to claim 1, wherein the concave groove is a peripheral groove of a diameter greater than the diameter of the cutting lips and which is open on the face of the ring directed towards the shank.

3. The surgical drill bit type cutting tool according to claim 1, wherein the inner surface of the ring has a shape of a body of revolution.

4. The surgical drill bit type cutting tool according to claim 1, wherein the active portion has at least two of the chip areas extending along at least part of the active portion, the chip areas being separated by the cutting lips.

5. The surgical drill bit type cutting tool according to claim 1, wherein a portion of the cutting lips locally includes a peripheral bulge, and the inner surface of the ring has a shape adapted to engage with the bulge.

6. The surgical drill bit type cutting tool according to claim 1, wherein the chip areas have, on a portion of the active portion surrounded by the ring, a helical orientation in a direction for driving a fluid present around the shank towards the active portion, when the cutting tool is rotated in its normal direction of rotation.

7. The surgical drill bit type cutting tool according to claim 1, wherein the ring comprises at least one portion forming a vane or a helix, oriented in a direction for driving a fluid present around the shank towards the active portion, when the cutting tool is driven in its normal direction of rotation.

8. The surgical drill bit type cutting tool according to claim 1, wherein the ring is removably mounted on the active portion.

9. The surgical drill bit type cutting tool according to claim 1, wherein the active portion is configured to receive the ring at a plurality of positions or to accommodate a plurality of rings.

10. The surgical drill bit type cutting tool according to claim 1, wherein the ring is fixedly mounted on the active portion.

11. The surgical drill bit type cutting tool according to claim 1, wherein the ring is made of metallic material.

12. The surgical drill bit type cutting tool according to claim 1, wherein the ring carries visible signs, suitable for giving information to a practitioner.

* * * * *